US012343549B2

(12) United States Patent
Lancaster

(10) Patent No.: US 12,343,549 B2
(45) Date of Patent: Jul. 1, 2025

(54) PREDICTIVE DIAGNOSTIC SYSTEM FOR A DISTRIBUTED POPULATION OF AUTOMATED EXTERNAL DEFIBRILLATOR DEVICES

(71) Applicant: KONINKLIJKE PHILIPS N.V., Eindhoven (NL)

(72) Inventor: Gregory James Lancaster, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 930 days.

(21) Appl. No.: 17/284,035

(22) PCT Filed: Oct. 18, 2019

(86) PCT No.: PCT/EP2019/078330
§ 371 (c)(1),
(2) Date: Apr. 9, 2021

(87) PCT Pub. No.: WO2020/083761
PCT Pub. Date: Apr. 30, 2020

(65) Prior Publication Data
US 2021/0379392 A1    Dec. 9, 2021

Related U.S. Application Data

(60) Provisional application No. 62/749,173, filed on Oct. 23, 2018.

(51) Int. Cl.
*A61N 1/39* (2006.01)
*G16H 40/40* (2018.01)
(Continued)

(52) U.S. Cl.
CPC ......... *A61N 1/3904* (2017.08); *A61N 1/3931* (2013.01); *G16H 40/40* (2018.01); *G16H 40/63* (2018.01); *G16H 40/67* (2018.01)

(58) Field of Classification Search
CPC .... A61N 1/3904; A61N 1/3931; G16H 40/63; G16H 40/67; G16H 40/40
See application file for complete search history.

(56) References Cited

U.S. PATENT DOCUMENTS 6,370,428 B1 * 4/2002 Snyder ................ A61N 1/3904
607/5
2014/0266718 A1    9/2014 Bongberg et al.
(Continued)

FOREIGN PATENT DOCUMENTS

WO    2004112900 A1    12/2004
WO    2011029101 A1    3/2011
WO    2018069040 A1    4/2018

OTHER PUBLICATIONS

PCT/EP2019/078330 ISR & WO, Jan. 7, 2020, 14 Pages.

*Primary Examiner* — Jennifer Pitrak McDonald
*Assistant Examiner* — Moussa Haddad

(57) ABSTRACT

A predictive diagnostic system (10) for a distributed population of automated external defibrillator (AED) devices comprises a plurality of AEDs (12) and a remote service provider (RSP) computer (14) configured to receive and transmit information pertaining to periodic AED self-tests. Each AED ($12_1$ to $12_N$) is provided with a controller for testing a readiness of the AED according to a self-test protocol. The RSP computer (i) analyzes self-test result data that includes functional measurement values of the periodic self-tests and which includes data from at least one failed AED ($12_{N-2}$ to $12_N$) of the plurality, (ii) identifies an indicator of an impending fault or failure predictive of an impending AED device fault or failure in at least one non-failed AED ($12_A$) based on the analyzed data, and (iii) remotely modifies the self-test protocol of a sub-set ($12_A$) of (Continued)

the plurality of AEDs, based on the indicator, to pre-empt an occurrence of a self-test failure in the AED devices of the sub-set.

12 Claims, 4 Drawing Sheets

(51) Int. Cl.
*G16H 40/63* (2018.01)
*G16H 40/67* (2018.01)

(56) References Cited

U.S. PATENT DOCUMENTS

| | | |
|---|---|---|
| 2015/0321010 A1 | 11/2015 | Marnfeldt |
| 2015/0321020 A1 | 11/2015 | Gumbrell |
| 2016/0067510 A1* | 3/2016 | Norton ................. A61N 1/3975 607/5 |
| 2016/0274162 A1* | 9/2016 | Freeman ................... A61N 1/39 |
| 2018/0001097 A1* | 1/2018 | Delisle ................. A61N 1/3993 |
| 2018/0296848 A1 | 10/2018 | Powers et al. |
| 2019/0232070 A1* | 8/2019 | Lancaster ............ A61N 1/3993 |
| 2019/0349435 A1* | 11/2019 | Durrant ................... H04L 41/20 |

\* cited by examiner

PREDICTIVE DIAGNOSTIC SYSTEM FOR A DISTRIBUTED POPULATION OF AUTOMATED EXTERNAL DEFIBRILLATOR DEVICES

CROSS-REFERENCE TO PRIOR APPLICATIONS

This application is the U.S. National Phase application under 35 U.S.C. § 371 of International Application No. PCT/EP2019/078330, filed on Oct. 18, 2019, which claims the benefit of U.S. Provisional Patent Application No. 62/749,173 filed on Oct. 23, 2018. These applications are hereby incorporated by reference herein.

BACKGROUND

The present embodiments relate generally to automated external defibrillator (AED) devices and more particularly, to a predictive diagnostic system for a distributed population of AED devices and a method thereof.

Cardiac arrest, ventricular fibrillation and cardiac arrhythmia are life-threatening heart conditions that require immediate cardiopulmonary resuscitation (CPR) and defibrillation to increase one's chances of survival. Defibrillation is a treatment that involves the delivery of an electric shock that allows reestablishment of the normal contraction rhythms of the heart.

Automated external defibrillators (AEDs) comprise easy-to-use, accessible, portable devices that are used to deliver defibrillation treatments. AEDs are usually deployed for long periods in public spaces, such as in schools, parks, residential areas, ambulances, and even police vehicles, in order to immediately respond to cardiac emergencies occurring in a public place. It is thus essential that deployed AEDs are always functional and ready for use in case of such emergencies.

Most AEDs are equipped with self-diagnosing, or self-testing, functions in order to periodically and automatically determine the usability of the AED while in deployment. Typically, alarms are generated based on the results of the self-testing to notify the appropriate party regarding, for example, the need for AED maintenance or repair.

In particular, traditional automated external defibrillator devices rely on an on-board self-test to verify the readiness of the device for clinical usage. The on-board self-test operates by periodically comparing measurement parameters of various components and/or subsystems of the AED to defined functional limits. In other words, traditional AEDs rely on the periodic self-test to identify if an AED device is capable of performing essential functions for diagnosis and therapy delivery. The self-test occurs by the AED device periodically exercising its internal circuitry and taking measurements of functional parameters, e.g. voltage, timing, current, impedance, noise, etc. The measurements are compared against defined limits in the AED device software, and the AED device alerts the user, e.g., via an audible alarm and/or displayed message, when a measurement exceeds a defined limit or limits. In addition, the AED device functionality may be disabled unless and until the error state is cleared, e.g., with a reboot of the AED device. While an AED device is generally effective at detecting device faults when the device is in a standby mode, there is a risk that a failure occurs during patient use and disadvantageously impacts the outcome of a patient therapy, i.e., an emergency resuscitation or other patient therapy.

One disadvantage of the traditional on-board self test is that the traditional self-test notifies AED device users of a failure or fault after the occurrence of the failure or fault, thus leaving the affected device in a state where it is unusable for a period of time. This has the adverse potential to render the affected AED device unavailable when needed for an emergency patient therapy use. One way that traditional AEDs deal with this problem is to provide a tiered fault alerting protocol. For example, a typical AED will issue an advisory alert if the battery is low but still able to operate the AED for a limited time. The same AED will subsequently issue a failure alert if the battery becomes too low to operate the device.

Accordingly, an improved AED self-test system and method for overcoming the problems in the art are desired.

SUMMARY

In accordance with one embodiment, a predictive diagnostic system for a distributed population of automated external defibrillator (AED) devices comprises a plurality of AEDs and a remote service provider computer. Each AED comprises an automated self-testing controller, a memory storage location, and a bi-directional transceiver. The automated self-testing controller is configured for testing a readiness of the respective AED via an AED self-test on a periodic basis. The memory storage location is configured for storing software instructions, executable by the automated self-testing controller, the software instructions including a protocol for executing the AED self-test. The memory storage location is further for storing (a) functional measurement values obtained via the AED self-test and (b) an AED self-test result. The bi-directional transceiver is configured to transmit the functional measurement values and the AED self-test result and to receive software instructions including a second protocol for executing a second AED self-test. The automated self-testing controller is further configured to automatically replace the protocol with the second protocol in the memory storage location.

The remote service provider computer comprises a processor, a bi-directional transceiver configured to receive and transmit information that pertains to the periodic AED self-tests of the plurality of AEDs, and a database. The remote service provider computer is programmed (i) to analyze the AED functional measurement values and the self-test results, wherein the AED self-test results further include data from at least one failed AED of the plurality of AEDs, (ii) to identify at least one indicator of an impending fault or failure that is predictive of an impending AED fault or failure in a sub-set of the plurality of AEDs based on the analyzed periodic AED self-test result data, and (iii) to obtain the second protocol for executing the second AED self-test of a sub-set of the plurality of AED devices, based upon the identified at least one indicator to pre-empt an occurrence of a failure outcome of an AED self-test in the AEDs of the sub-set of the plurality of AEDs. The remote service provider computer is further programmed (iv) to transmit the software instructions including the second protocol for executing the second AED self-test to only the sub-set of the plurality of AEDs.

In another embodiment, the predictive diagnostic system includes wherein the indicator comprises a data signature of functional measurement values of the at least one AED of the plurality of AEDs which has failed. In addition, the remote service provider computer determines the sub-set of the plurality of AEDs in response to at least one non-failed AED of the plurality of AEDs having a data signature matching, by at least a given percentage (e.g., in a range of 95% to 99%), the data signature of the at least one AED which has failed.

In yet another embodiment, the predictive diagnostic system includes wherein the indicator comprises a data trend of functional measurement values of the at least one AED of the plurality of AEDs which has failed. In addition, the remote service provider computer determines the sub-set of the plurality of AEDs in response to at least one non-failed AED of the plurality of AEDs having a data trend matching, by at least a given percentage (e.g., in a range of 95% to 99%), the data trend of the at least one AED which has failed.

In still another embodiment, the remote service provider computer analyzes the AED self-test result data via at least one predictive algorithm that comprises at least one selected from the group consisting of (i) a machine learning classification algorithm, (ii) a multi-dimensional outlier detection algorithm, and (iii) a time series performance degradation algorithm. The machine learning classification algorithm can include, for example, a Classification and Regression Tree, CART, algorithm, and/or a Neural Networks algorithm, and/or Bayes classifiers. In addition, the multi-dimensional outlier detection algorithm can include, for example, a Mahalanobis Distance method. Furthermore, the time series performance degradation algorithm includes at least a time series method of analyzing a trend in self-test measurement values to predict a time when a value will degrade to a point where the value no longer meets one or more specification limits.

According to another embodiment, the remote service provider computer transmitting further comprises transmitting, via the bi-directional transceiver of the remote service provider computer and a corresponding bi-directional communications path, one or more of (i) a notification, self-test protocol command, or instruction directly to a respective AED of the sub-set of the plurality of AEDs to signal an alert at the respective AED of a corresponding impending fault or failure, and (ii) a notification (e.g., email, sms text message, cell phone app, or an automated voice message) directly to a registered administrator of the respective AED of the corresponding impending fault or failure.

According to yet another embodiment, the functional measurement values relate to an electrical resistor component in the AED. In addition, the functional measurement values comprise voltage measurements across the resistor, wherein the voltage measurements across the resistor indicate a likelihood of impending failure after a subsequent given number of energy pulses applied during a corresponding self-test of a given AED. Furthermore, the remote service provider computer analyzes the functional measurement values for a degrading voltage measurement over time, which by itself would not result in a self-test failure outcome, to identify the at least one indicator of an impending fault or failure.

According to still another embodiment, the remote service provider computer is further programmed to analyze via applying at least one predictive algorithm to both past and updated sets of periodic self-test result data of the plurality of AEDs and to identify at least one AED in the sub-set (i.e., having a high likelihood of failure greater than a given percentage (e.g., in a range of 95% to 99%) for failure) as approaching failure based on the applied predictive algorithms.

In another embodiment, a method for predictive diagnostics in a distributed population of automated external defibrillators (AEDs) comprises the steps of providing a plurality of AEDs; analyzing AED functional measurement values and self-test result data received from the plurality of AEDs; identifying at least one indicator of an impending fault or failure that is predictive of an impending AED fault or failure in at least one non-failed AED of the plurality of AEDs based on the analyzed periodic AED self-test result data; modifying the protocol for executing the AED self-test of a sub-set of the plurality of AEDs based upon the identified at least one indicator to pre-empt an occurrence of a failure outcome of the AED self-test in the AEDs of the sub-set of the plurality of AEDs (i.e., the AEDs that have not yet failed, but which have been determined to have a high likelihood of failure); transmitting software instructions including the modified protocol (or second protocol) for executing a second AED self-test to only the sub-set of the plurality of AEDs; and operating the sub-set of the plurality of AEDs using the transmitted software instructions. Each AED comprises (i) an automated self-testing controller for testing a readiness of the respective AED device, via at least one AED self-test, on a periodic basis, (ii) a memory storage location for storing software instructions, executable by the automated self-testing controller, that include at least a protocol for executing the at least one AED self-test, the memory storage location further for storing (ii)(a) functional measurement values obtained via the at least one AED self-test and (ii)(b) at least one AED self-test result, and (iii) a bi-directional transceiver configured to transmit the functional measurement values and the AED self-test result and to receive software instructions including a second protocol for executing the second AED self-test, the controller operable to automatically replace the protocol with the second protocol in the memory storage location.

The analyzing is accomplished via a remote service provider computer provided with a processor, a bi-directional transceiver configured to receive and transmit information that pertains to the periodic AED self-tests of the plurality of AEDs, AED functional measurement values and self-test result data received from the plurality of AEDs, and a database. The AED self-test result data further includes data from at least one failed AED of the plurality of AEDs. The steps of identifying the at least one indicator and modifying the protocol for executing the AED self-test of the sub-set, based on the at least one indicator, are accomplished via the remote service provider computer. The second protocol is configured to pre-empt an occurrence of a failure outcome of an AED self-test in the AED devices of the sub-set of the plurality of AED devices (i.e., the AED devices that have not yet failed, but which have been determined to have a high likelihood of failure).

According to yet another embodiment, a non-transitory computer-readable medium is embodied with a computer program of instructions executable by a computer for carrying out the method of predictive diagnostics in a distributed population of automated external defibrillator (AED) devices, as discussed herein.

In another embodiment, an automated external defibrillator (AED) for use in a predictive diagnostic system for a distributed population of AEDs comprises (i) an automated self-testing controller for testing a readiness of the AED, via a first AED self-test, on a periodic basis, (ii) a memory storage location for storing software instructions, executable by the automated self-testing controller, that include a first protocol for executing the first AED self-test, the memory storage location further for storing (ii)(a) functional measurement values obtained via the first AED self-test and (ii)(b) at least one AED self-test result, (iii) a bi-directional transceiver configured to transmit the functional measurement values and the AED self-test result and to receive software instructions including a second protocol for executing a second AED self-test, and (iv) an output controllably connected to the controller and configured to indicate which of the first and the second AED self-test is in use.

In a further embodiment, the AED for use in the predictive diagnostic system for a distributed population of AEDs includes wherein the output comprises one selected from the group of a defibrillator display, an audible output and a visual status light. In addition, the AED further comprises an information button input in communication with the controller, the controller configured to provide detailed AED self-test information relating to the first and the second AED self-test to the user via the output.

In yet another embodiment, the AED further includes wherein the functional measurement values relate to a resistor (R) of an AED, wherein the functional measurement values comprise voltage measurements across the resistor (R), wherein the voltage measurements across the resistor indicate a likelihood of impending failure after a subsequent given number of energy pulses applied across the resistor during a corresponding self-test of a given AED. According to another embodiment, the AED includes wherein the output further indicates that the AED is ready for use and that user action to contact an AED service provider is requested.

According to the embodiments of the present disclosure, the predictive diagnostic system or predictive AED device health monitoring system advantageously augments the traditional on-board self test of AED devices with an advanced warning of an impending failure (or one or more impending failures). The predictive diagnostic system further advantageously allows AED users to address imminent failures, prior to actual occurrences of the failures, with maintenance, repair, or replacement in a controlled and managed fashion, such as identifying a backup device, with minimal risk to adversely impacting a patient use need.

The embodiments of the present disclosure further advantageously solve a problem with traditional on-board self tests of AED devices by providing a predictive AED device health monitoring system configured to collect self test diagnostic data from a population of similar AEDs, including AEDs which have failed, and to apply statistical methods and/or learning algorithms to the population of AEDs to identify specific AEDs (i.e., a sub-set or sub-population) of the population of AEDs which possess a high likelihood of an imminent failure.

The embodiments of the present disclosure also advantageously augment the traditional on-board self-test with a secondary, predictive device health monitoring system. According to one embodiment, data from the on-board periodic self-tests of a plurality of AEDs is uploaded into a remote central server and stored in a database. The uploaded data consists of data from an entire population of similar AED devices. The remote server applies predictive algorithms such a multi-dimensional outlier detection, time series performance degradation, and machine learning classification to the population of data (i.e., stored in the database), including AED devices in the population that have failed or experienced faults. One advantageous use of the predictive algorithms is to identify non-failed AEDs in the population that are approaching failure, or have a data "signature" (or identifier) similar to within a given percentage of a corresponding data signature, of those AEDs in the population which have already failed. Responsive to identifying a non-failed AED in the population as approaching a fault or failure, based on the "signature" or identifier, in one embodiment, the device health monitoring system then provides notification of the impending fault or failure, based on the "signature" or identifier, via (i) communication to the affected AED device to signal an alert, and/or (ii) communication to a registered administrator of the affected AED device.

The inventors have discovered that the improved systems and apparatus described herein offer particular benefits for portable defibrillators which may reside in a standby state for long periods of time between uses. Long after such defibrillators are placed into operation, a mode of failure may arise which was not predicted (or predictable) when the defibrillators were designed, and hence for which the original self-testing protocol was not designed to capture. The present invention enables the identification and possible associated predictions of such a failure mode. Moreover, the present invention enables the adjustment of a self-testing protocol to detect the discovered failure mode, the adjustment being only in that sub-population of defibrillators which may be susceptible to the failure mode. Other defibrillators which are not so susceptible thus remain unaffected by an adjustment and by the associated reduced battery life incurred because of the enhanced self-test.

Still further advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1:
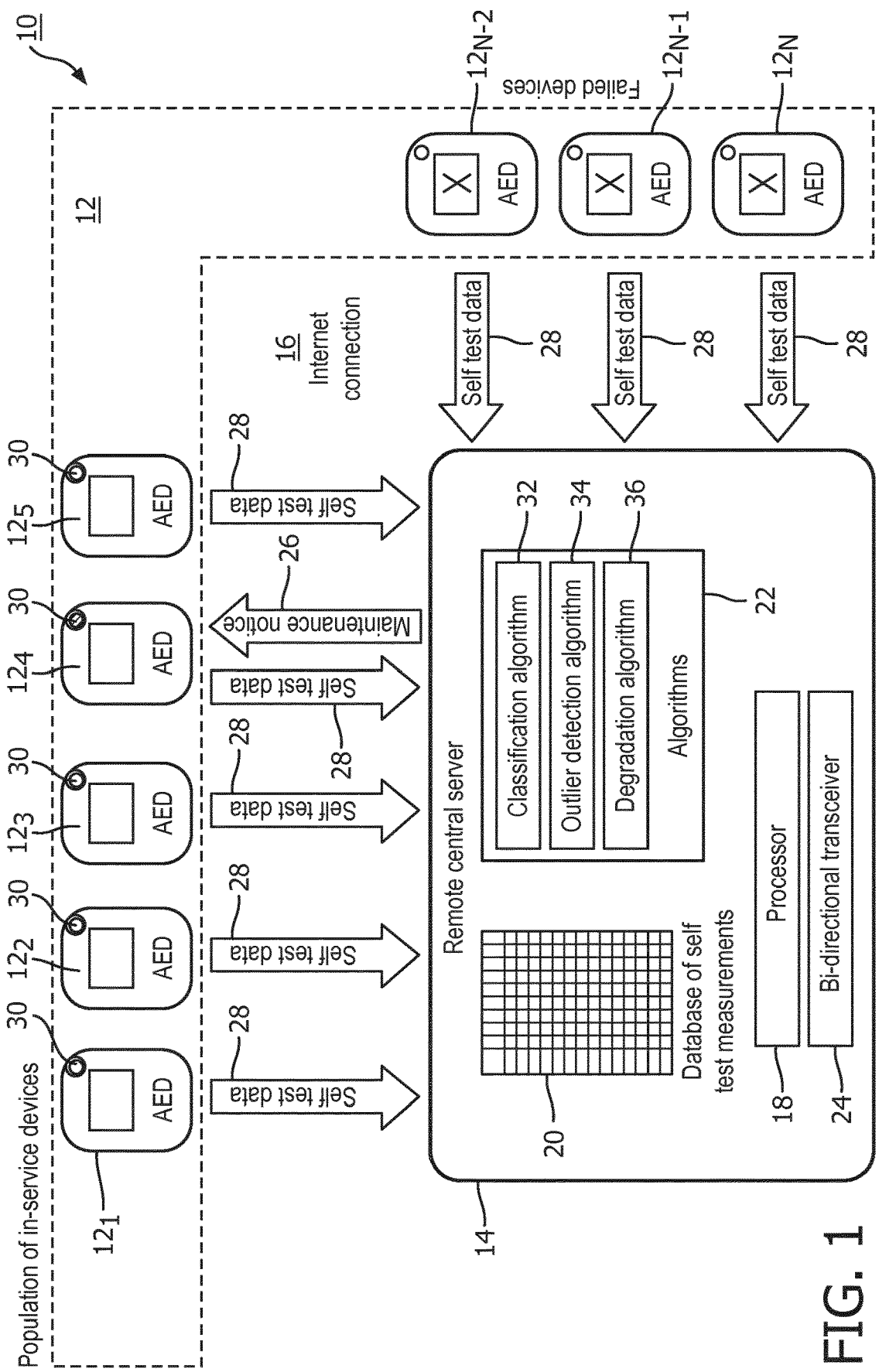
FIG. 1 is a block diagram view of a predictive diagnostic system or device health monitoring system for a distributed population of automated external defibrillator (AED) devices according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

The following are definitions of terms as used in the various embodiments of the present invention.

The term "self-test" or "diagnostic test" as used herein refers to the AED's automated self-diagnostic function for determining the operability state of the AED based on the condition of its components. The diagnostic test includes, but is not limited to, a battery test for determining the remaining power available to the AED, a CPU state test for determining if the AED's internal registry and memory are accessible, a memory space test for determining the AED's free memory, an electrodes integrity test for determining usability of electrodes based on electrode expiration date or a sensed condition of the electro-gel, an ECG calibration test for ensuring ECG monitoring function of the AED is accurate, or a sensed expiration of shelf life for device or accessories.

For example, with respect to AED self-tests outcomes, a non-fatal fault, such as "low battery" fault, indicates that the AED device may be used if needed during an emergency even in the presence of the fault. In comparison, a fatal fault indicates that the AED device is completely inoperable for emergency use.

The term "operability state" as used herein refers to the AED's usability condition determined by a diagnostic test performed at a specific time. The AED operability state relates to all the parameters tested and determined by the diagnostic test. These parameters may include battery level, CPU state, memory space status, electrodes integrity, ECG calibration status, among others. The AED's operability state includes a standard operable state and an alert state, wherein the alert state is determined by matching the determined operability state with stored alert states in the AED memory.

The term "alert" as used herein refers to any action the system may execute in response to a determined operability state of the AED to call immediate attention towards the AED for device maintenance and repair. Examples of alerts are prompting visual indicators, audio alarms, and vibratory alarms, sending messages alerting service personnel and community administration, or any combination thereof, among others.

The term "database" as used herein refers to a collection of data and information organized in such a way as to allow the data and information to be stored, retrieved, updated, and manipulated and to allow them to be presented into one or more formats such as in table form or to be grouped into text, numbers, images, and audio data. The database typically resides in computer memory that includes various types of volatile and non-volatile computer memory. "Database" as used herein also refers to conventional databases that may reside locally or that may be accessed from a remote location, e.g., remote network servers. The term "database" as used herein may also refer to a segment or portion of a larger database, which in this case forms a type of database within a database. Memory wherein the database resides may include high-speed random access memory or non-volatile memory such as magnetic disk storage devices, optical storage devices, and flash memory. Memory where the database resides may also comprise one or more software for processing and organizing data received by and stored into the database.

Terms referring to electrical components such as processors, clocks, memory, modules, inputs, outputs, display, systems, transceivers, power sources, and the like are understood to be circuit hardware as commonly understood in the art. Such circuit components may be integrated together in whole or in part such as in ASICS, hardware microprocessors, Field Programmable Gate Arrays (FPGA), random access memory, fixed memory modules, and the like. The system comprising the circuit components may be under the control of software instructions that reside in memory and are executed by various computing hardware in the AED.

As indicated herein above, traditional automated external defibrillator (AED) devices rely on an on-board self-test to verify the readiness of the device for clinical usage. The self-test operates by periodically comparing measurement parameters of various components and/or subsystems of the AED to defined functional limits.

According to the embodiments of the present disclosure, with self-test data uploaded to a remote service provider computer or remote central computer, the remote service provider computer applies predictive algorithms to the self-test data to identify AEDs that have a high likelihood of imminent failure. In one embodiment, responsive to identifying one or more affected AEDs, the remote service provider computer is configured to (i) send a maintenance alert to the affected AEDs and/or (ii) provide alternative communication to an AED administrator of the affected AEDs. In this manner, such affected AEDs can be pre-emptively removed from service for maintenance or repair prior to an actual occurrence of a failure and thereby significantly reduce the likelihood of an unexpected failure to impact the corresponding device's availability for a patient use.

In operation, the predictive device health monitoring system according to the embodiments of the present disclosure collects self-test diagnostic data from a population of similar AEDs, including AED devices within the population that have failed. The predictive device health monitoring system is configured to apply statistical methods and/or learning algorithms to the self-test diagnostic data of the population of AEDs to identify specific AEDs in the population of AEDs that have a high likelihood of an imminent failure as will be discussed further herein. As used herein, the term "imminent" shall be interpreted to mean a failure predicted to occur within 3 to 6 months. The accuracy of the one or more algorithms likely limits the resolution of a prediction to a few months. Once a failure has been predicted for a device with high probability, the remote modifications of the AED self-test protocol and/or notification would then be provided only to a corresponding identified sub-set of AED devices in the population.

With reference now to FIG. 1, a block diagram view illustrates a predictive diagnostic system or device health monitoring system for a distributed population of automated external defibrillators (AEDs) according to an embodiment of the present disclosure. The device health monitoring system 10 comprises a population, generally indicated by reference numeral 12, of AEDs in distribution, individually indicated via reference numerals $12_1$, $12_2$, ... $12_{N-1}$, $12_N$, where N is an integer number of devices in the population. The device health monitoring system 10 further includes a remote central server (RCS) or remote service provider computer 14 and a communication link 16, such as a wireless internet connection or other wireless connection, transceiver or the like, between the RCS 14 and the population of AEDs 12. The communication link 16 is configured for transferring data from each AED device and delivering commands to specific ones of affected AED devices. It should be noted that the population of AEDs may have minor variations in physical characteristics that could be used to identify subgroups for later self-test modification. The remote central server 14 can further include a database of all of those variations. The minor variations may include not only device manufacture date, but also changes to components (such as resistors, assemblers, etc.) that might impact the prediction. For example, if an electrical resistor component at issue was manufactured by a certain manufacturer, and the experienced failure occurs only in those resistors, then the modified self-test should be sent only to devices in the population having that component from those manufacturing lots. One advantageous goal would be avoiding excessive self-testing modifications to those sub-populations that don't need them. The commands and/or self-testing modifications may include, for example, a command to issue an alert that attention is needed. Such an alert could comprise an audible alert (e.g., beeping or other audible message) or a visual alert (e.g., a flashing light or other flashing display). The commands and/or self-testing modifications could also include one or more additional command to run or execute specific self-diagnostic tests at a greater frequency or in a different sequence of the self-diagnostic tests.

The remote central server 14 includes a processor 18, a database 20, a series of algorithms 22, and a bi-directional transceiver 24. The database 20 is configured to store (a) self-test measurement data received from each AED device and (b) the series of algorithms 22. The series of algorithms 22 are adapted to analyze the self test measurement data and identify patterns or trends that indicate a high likelihood of impending failure in a given one or more AED device. The remote central server 14 is also configured to provide a mechanism to alert an affected one or more AED directly (e.g., by providing a maintenance notice, as indicated via arrow 26 in FIG. 1, to AED $12_4$), and/or through an administrator, that the affected one or more AED should be serviced.

Each AED in the given population of distributed devices executes a periodic self diagnostic test, and sends the functional measurement values from the respective periodic self diagnostic test to the remote central server (RCS) 14, as indicated via arrows 28 in FIG. 1. The functional measurement values are entered in the database 20 that contains the self diagnostic history for each AED (i.e., devices $12_1$ to $12_N$) in the population, including both AEDs in service (e.g., devices $12_1$ to $12_5$) and those which have failed and been removed from service (e.g., devices $12_{N-2}$ to $12_N$, as illustrated with an "X" in FIG. 1). The database 20 also includes information regarding the functional or failed status of each AED in the population, which may also be indicated directly on each respective AED via a suitable status indicator 30 (e.g., an LED capable of multiple different colors and for which a given color is indicative of a given status). As shown in FIG. 1, the in-service AED 124 has experienced a non-fatal fault and so its status indicator 30 is illustrated as different from the other in-service AED devices. In addition, as shown in FIG. 1, a maintenance notice indicated via arrow 26 is sent to AED $12_4$.

In one embodiment, the predictive diagnostic system 10 for a distributed population of automated external defibrillator (AED) devices comprises a plurality of AEDs 12 and a remote service provider computer 14. Each AED is provided with an automated self-testing controller (e.g., processor 126, FIG. 3), a memory storage location (e.g., memory storage 116, FIG. 3), and a bi-directional transceiver (106, FIG. 3). The automated self-testing controller 126 is configured for testing a readiness of the respective AED, via an AED self-test, on a periodic basis. The memory storage location 116 is configured for storing software instructions, executable by the automated self-testing controller 126, the software instructions including a protocol for executing the AED self-test. The memory storage location 116 is further for storing (a) functional measurement values obtained via the AED self-test and (b) an AED self-test result. The bi-directional transceiver 106 is configured to transmit the functional measurement values and the AED self-test result and to receive information that pertains to one or more of the periodic AED self-tests, wherein the information comprises at least software instructions including a second protocol for executing a second AED self-test. The automated self-testing controller is further configured to automatically replace the protocol with the second protocol in the memory storage location.

In addition, the remote service provider computer 14 comprises a bi-directional transceiver 24 configured to receive and transmit information that pertains to the periodic AED self-tests of the plurality of AEDs (i.e., devices $12_1$ to $12_N$). The remote service provider computer 14 is programmed (i) to analyze the AED functional measurement values and the self-test results, wherein the AED self-test results further include data from at least one failed AED of the plurality of AEDs, (ii) to identify at least one indicator of an impending fault or failure that is predictive of an impending AED device fault or failure in a sub-set of the plurality of AEDs based on the analyzed periodic AED self-test result data, and (iii) to obtain the second protocol for executing the second AED self-test of a sub-set of the plurality of AEDs (e.g., in-service AED device $12_4$), based upon the identified at least one indicator. As discussed, the AED self-test result data received from the plurality of AEDs includes functional measurement values of periodic AED self-tests and further includes data from at least one failed AED device (e.g., devices $12_{N-2}$ to $12_N$, as illustrated with an "X" in FIG. 1) of the plurality of AEDs. Obtaining the second protocol for executing the second AED self-test in the sub-set of the plurality of AED devices (e.g., as illustrated via arrow 26, FIG. 1), based upon the identified at least one indicator, pre-empts an occurrence of a failure outcome of an AED self-test in the AEDs of the sub-set of the plurality of AEDs. The remote service provider computer is further programmed (iv) to transmit the software instructions including the second protocol for executing the second AED self-test to only the sub-set of the plurality of AEDs.

In one embodiment, the indicator comprises a data signature of functional measurement values of the at least one AED of the plurality of AEDs which has failed (e.g., devices $12_{N-2}$ to $12_N$). In this instance, the remote service provider computer 14 determines the sub-set of the plurality of AEDs in response to at least one non-failed AED (e.g., in-service AED device $12_4$) of the plurality of AEDs having a data signature matching, by at least a given percentage (e.g., in a range of 95% to 99%), the data signature of the at least one AED (e.g., devices $12_{N-2}$ to $12_N$) which has failed.

In another embodiment, the indicator comprises a data trend of functional measurement values of the at least one AED device (e.g., devices $12_{N-2}$ to $12_N$) of the plurality of AEDs which has failed. In this instance, the remote service provider computer 14 determines the sub-set of the plurality of AEDs in response to at least one non-failed AED (e.g., in-service AED device 124) of the plurality of AEDs having a data trend matching, by at least a given percentage (e.g., in a range of 95% to 99%), the data trend of the at least one AED (e.g., devices $12_{N-2}$ to $12_N$) which has failed.

Referring again to FIG. 1, at the remote central server 14, the series of algorithms 22 are run (i.e., executed) periodically on the received self-test data to learn characteristic patterns of measurements (i.e., functional measurement values) from data of failed AEDs (e.g., devices $12_{N-2}$ to $12_N$), and to detect similar patterns in the self-test functional measurement value data of AEDs that have not yet failed, but which may have a strong indication of failure or an indication of failure greater than or equal to an impending failure threshold. In other words, the remote central server 14 actively searches for an occurrence of one or more characteristic patterns, derived from the self-test functional measurement value data of the failed AEDs (e.g., devices $12_{N-2}$ to $12_N$), within the self-test functional measurement value data of AEDs (e.g., devices $12_1$ to $12_5$) that have not yet failed. The algorithms 22 are otherwise referred to herein as machine learning algorithms, and include one or more of algorithms as discussed further herein below. In addition, the remote service provider computer 14 is programmed to analyze further via applying at least one predictive algorithm to both past and updated sets of periodic self-test result data of the population of AEDs and to identify at least one AED or sub-set of AEDs (i.e., having a high likelihood of failure greater than a given percentage (e.g., in a range of 95% to 99%) for failure) as approaching failure based on the applied predictive algorithms.

A first method or machine learning algorithm 32 is the Classification and Regression Tree (CART). CART is used to predict a specific classification (e.g., failed or functional) for an object (i.e., in this case an AED device) based on high dimensional data for the object.

A second method or machine learning identification algorithm 34 for identification of impending failure is to analyze for statistical outliers in multi-variate data (i.e., in this case, a database of functional measurement values of AED devices of the population). The Mahalanobis Distance method is an example of such an algorithm.

A third method or machine learning algorithm 36 for prediction of impending failure is degradation analysis, a time series method of analyzing the trend in measurement values (i.e., database of functional measurement values of AED devices of the population) to predict a time when the value will degrade to the point it no longer meets the specification limits.

The machine learning algorithms can assess their predictive power through cross-validation methods. Cross validation is a method to quantify the accuracy of an algorithm. The available data is randomly divided into two sets. The algorithm "learns" from one data set (e.g., half of the available data), and then is used to predict the result of the other "validation" data set. The predictions are compared against the actual validation data results to understand the accuracy of the prediction, e.g., the algorithm detects 95% of a failure type before the failure occurs. Cross validation is commonly used to assess the predictive power of algorithms that "learn" from the data.

Upon identification of an AED with a high likelihood of failure (i.e., an impending failure threshold has been met or exceeded by the AED device), in one embodiment the device health monitoring system 10, via the remote central server 14, remotely triggers a "readiness for use" alarm in the affected AED (e.g., in-service AED 124). The "readiness for use" alarm is indicative that the AED is not ready for use, for example, similar to an occurrence of a device and/or component failure. In this case, the affected AED would provide a similar type of user alert as it would upon an internal on-board self test failure. In another embodiment, the device health monitoring system 10, via the remote central server 14, remotely triggers a "maintenance required" message on the affected AED device, indicating that it is still fully functional but that a preventive maintenance need has been detected and that the AED should be serviced. In a further embodiment, the device health monitoring system directly notifies a registered manager of the affected AED device, e.g., through email or a cell phone app, that preventive maintenance is needed on the affected AED device.

In one embodiment, remotely modifying, or otherwise obtaining, the second protocol for executing the second AED self-test in the sub-set of the plurality of AEDs based upon the identified at least one indicator further comprises the remote service provider computer 14 transmitting, via the bi-directional transceiver 24 and a corresponding bi-directional communications path 16, one or more of (i) a notification, self-test protocol command, or instruction directly to a respective AED (e.g., in-service AED $12_4$) of the sub-set of the plurality of AEDs to signal an alert at the respective AED of a corresponding impending fault or failure, and (ii) a notification (e.g., email, sms text message, cell phone app, or an automated voice message) directly to a registered administrator of the respective AED device of the corresponding impending fault or failure. As noted previously herein, the population of AEDs may have minor variations in physical characteristics that could be used to identify subgroups for later self-test modification. The remote central server 14 further includes a database of all of those variations. The minor variations may include not only device manufacture date, but also changes to components (such as resistors, assemblers, etc.) that might impact the prediction. For example, if a resistor at issue was manufactured by a certain manufacturer, and the experienced failure occurs only in those resistors, then the modified self-test should be sent only to those devices in the population having the component from the corresponding manufacturing lots. As a result, excessive self-testing modifications to those sub-populations that don't need them is advantageously avoided. In addition, the commands and/or self-testing modifications may include, for example, a command to issue an alert that attention is needed. Such an alert could comprise an audible alert (e.g., beeping or other audible message) or a visual alert (e.g., a flashing light or other flashing display). The commands and/or self-testing modifications could also include one or more additional command to run or execute specific self-diagnostic tests at a greater frequency or in a different sequence of the self-diagnostic tests.

Furthermore, the acceptance limits for a measured parameter could be modified. Such commends and/or modifications and/or acceptance limits are transmitted, for example, via the software instructions with the second protocol for executing the second AED self-test to only the sub-set of the plurality of AEDs.

The embodiments of the present disclosure advantageously overcome disadvantages of the known AEDs. That is, when an AED experiences a failure in service, although the failure typically is detected by the on-board self test and the user is alerted, the user is left without an available AED device in the service location for a period of time while the affected device is returned to the manufacturer for service and a replacement device is received. This raises a small but tangible risk that the AED is needed for defibrillation therapy on a cardiac arrest patient during this reparation process. By predicting an AED device failure before an actual failure occurs, according to the embodiments of the present disclosure, pre-emptive maintenance service for an affected AED in the population of AEDs can be managed and controlled such that there is always an availability of a functional AED device at a given service location.

Figure 2:
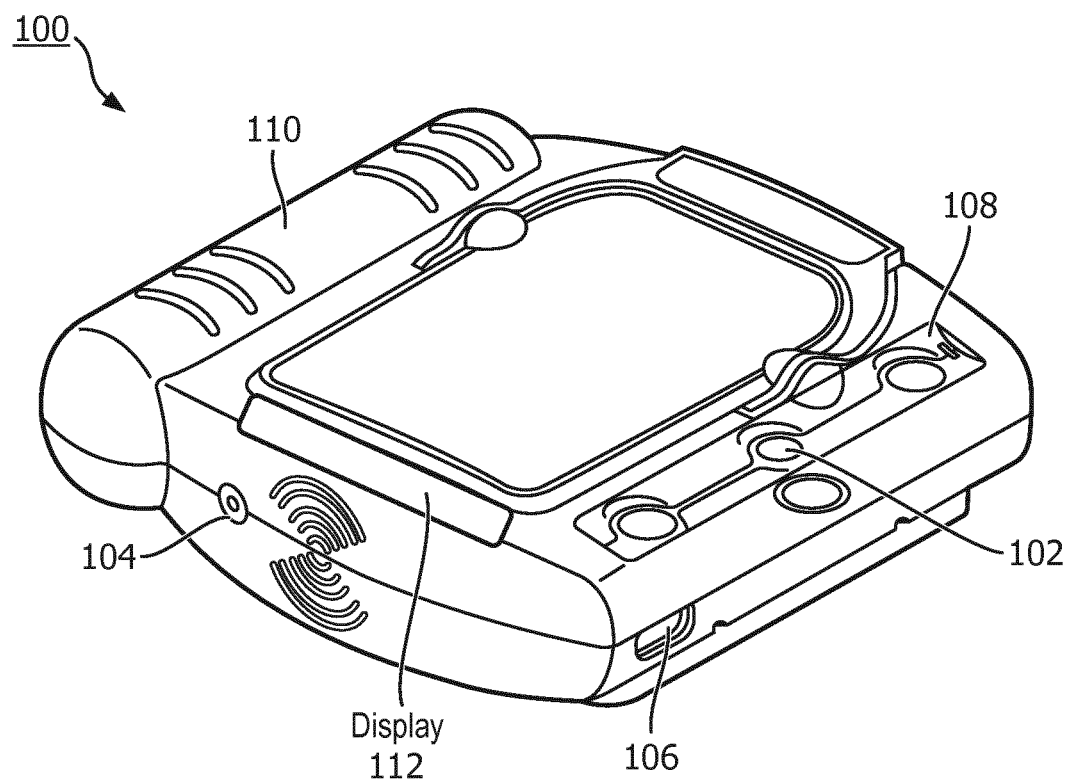
FIG. 2 is a perspective view of a defibrillator, such as an AED device, included within the distributed population of AED devices according to an embodiment of the present disclosure.

Referring now to FIG. 2, a perspective view is shown of a defibrillator 100, such as an AED ($12_1$ to $12_N$), included within the distributed population 12 of AEDs according to an embodiment of the present disclosure. In particular, FIG. 2 illustrates the external portion of a defibrillator or AED 100. The AED comprises a diagnosing system for determining an operability state of the AED, an alert system for activating an at least one alert based on the determined operability state, a communication system for sending the at least one alert to a remote device, and a processor for controlling the diagnosing system, the alert system, and the communication system.

Figure 3:
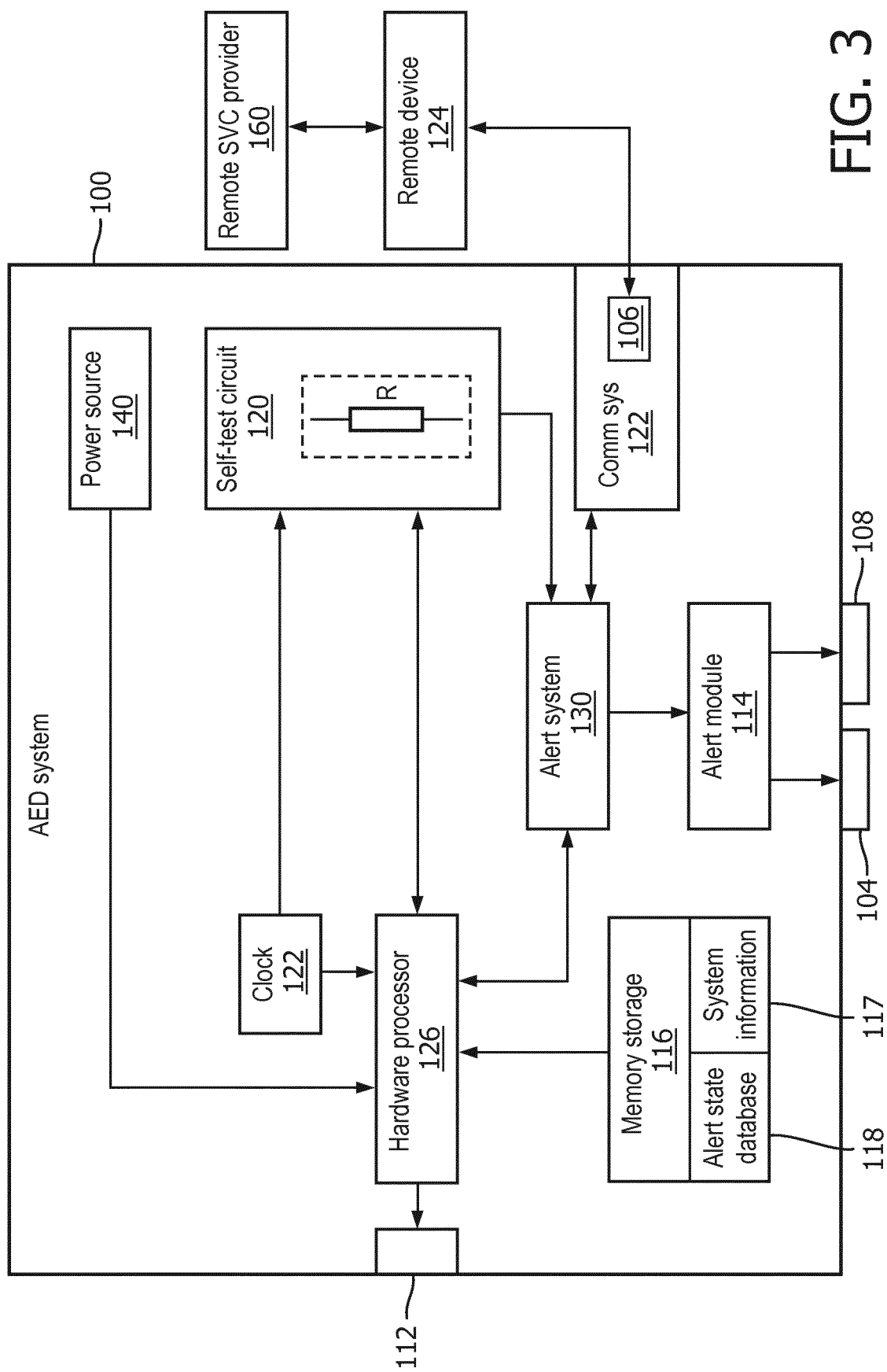
FIG. 3 is a block diagram view of the defibrillator of FIG. 2 according to an embodiment of the present disclosure.

With reference to FIGS. 2 and 3, the automated external defibrillator (AED) 100 device includes a housing 110, inside of which are circuits including a hardware processor or controller 126 and clock 122 configured to control an AED self-testing circuit 120. As will be described in more detail, hardware processor 126 periodically activates the self-testing circuit 120 during low-power standby conditions to conduct a diagnostic self-test. The self-test result is conveyed via an initial determination output to the user or a remote central server 14 (FIG. 1) or remote service provider (RSP) control station 160. The result is also stored in a memory 116/117. Upon a completion of the diagnostic self-test, the hardware processor 126 then returns the device to standby to conserve power.

AED 100 conveys a self-test result to the user via one or more of a defibrillator display 112, a self-test status audible output 104 such as a buzzer or beeper, and a self-test status visual output 108 such as an LED or LCD indicator light, all of which are disposed in communication with the self-test circuit 120. The outputs are preferably arranged on the housing 110 such that a user can easily hear or see indications relating to the result. In addition, AED 100 can convey, via one or more of the display, audible output, visual output, and/or an informational button (e.g., an i-button, as discussed further herein below), an indication of which of the first or the second AED self-test, according to the first or second protocol, as discussed herein, is in use.

In communication with hardware processor 126 is an AED informational button (i-button) 102 disposed on the exterior surface of housing 110. In addition, a bi-directional and wireless communications transceiver 106 is in controllable communication with hardware processor 126. Wireless transceiver 106 is configured to transmit a self-test fault alert responsive to a detected self-test fault. The transmission is directed to an external remote communicator device 124 and/or a remote central server 14 (FIG. 1) or remote service provider control station 160 (FIG. 3).

With reference now to FIG. 3, a block diagram view is shown of the defibrillator of FIG. 2 according to an embodiment of the present disclosure. The block diagram illustrates the internal components of a preferred AED 100. Hardware processor 126 provides for the central control of AED 100 functions and operates under control of clock 122. Software instructions for processor 126 may be stored in memory 116. A power source 140 provides power for the system and may comprise, for example, a rechargeable or primary battery.

Clock 122 and processor 126 also control the activation and conduct of self-test circuit 120. When not in use, AED 100 is in a low-power standby mode of operation, wherein the self-test circuit 120 periodically activates and tests various components of the device on a schedule. Low-voltage and battery components may be tested on a daily schedule. High-voltage defibrillation components may be tested on a bi-weekly or monthly schedule. Results (i.e., determinations) of self-tests are conveyed via an alert system 130 and alert module 114 to visual and audible outputs 104/108. Successful results are preferably indicated by silence and a ready for use indicator light. Unsuccessful results may be indicated by a beep and a rapidly flashing light. Optionally, test results may be displayed in text or graphic format at display 112.

In accordance with the embodiments herein, the inventor observed that an electrical resistor component (indicated in FIG. 3, via the letter "R" as illustrated within the self-test circuit 120) in an AED device was determined to have failed after a number of energy pulses that occurred during the self test of the AED device. However, the failure of the resistor was only detectable once catastrophic failure of the resistor occurred, thereby leaving the AED incapable of providing defibrillation therapy. The inventor further observed that an analysis of voltage measurements recorded in the affected AED device self tests prior to the catastrophic failure showed a degrading voltage measurement, which by itself did not result in a self test failure (i.e., corresponding to a catastrophic failure whereby the AED was rendered incapable of providing defibrillation therapy). In view thereof, the inventor of the device health monitoring system of the present disclosure further recognized that by algorithmically detecting this degrading voltage measurement in the functional characteristics of a self-test for AED devices not yet having failed, a notification can be provided to affected AED devices and/or the users of such AED devices. The notification comprises, for example, an indication of the need for a preventive maintenance action before a catastrophic failure of the resistor of a respective AED device (i.e., in response to having predicted an occurrence of impending failure in a non-failed AED device before it actually happens).

Accordingly, the AED self-tests include functional measurement values that relate to the resistor R of AED 100, wherein the functional measurement values comprise voltage measurements across the resistor. The voltage measurements across the resistor R are used to determine an indication of a likelihood of impending failure after a subsequent given number of energy pulses applied across the resistor during a corresponding self-test of the AED device 100. In addition, the remote central server 14 or remote service provider computer analyzes the functional measurement values for a degrading voltage measurement over time, which by itself would not result in a self-test failure outcome, to identify the at least one indicator of an impending fault or failure.

With reference still to FIG. 3, the wireless transceiver 106 is shown as a component of a communication system 122 that is in communication with processor 126 and alert system 130. Transceiver 106 is preferably bi-directional and may be of wireless (WiFi), telephonic, wired, or infrared (IR) function and the like. Transceiver 106 is configured to transmit not only a self-test failure alert responsive to an initial determination output of a failed self-test, but also self-test functional data, as discussed herein. In other words, the wireless transceiver is controllably coupled to the hardware processor, wherein the hardware processor and transceiver are configured to transmit self-test functional measurement data and/or fault alert responsive to an operation of the device self-test and/or responsive to a determination output of a failed self-test.

The transmission, via transceiver 106, is preferably directed to remote device 124 and/or a remote service provider control station 160 or a remote central server 14 (FIG. 1). Transceiver 106 is preferably configured to receive an acknowledgement of the transmission from the remote device/system, whereupon the processor 126 may modify a protocol for executing the AED device self-tests to pre-empt an occurrence of a failure outcome of an AED self-test of the AED device, in response to that AED device having been determined to have a high likelihood for imminent failure.

Acknowledgement may also cause processor 126 to indicate that corrective action is ongoing by third parties at display 112 or the like. FIG. 3 illustrates remote device 124 optionally as a relay between AED 100 transceiver 106 and remote service provider control station 160 (or remote central server 14, FIG. 1). In this embodiment remote device 124 may be configured to covert for example a received infrared signal from transceiver 106 to a wireless RF signal for further transmission to RSP control station 160. In other embodiments, the remote service provider control station 160 initiates a service action based on a receiving of the self-test fault alert, and/or the service action comprises sending corrective material to the location of the defibrillator, and/or the service action comprises dispatching a technician to the location of the defibrillator.

As discussed, the defibrillator has an automatic self-testing circuit which provides a periodic self-test of components while the AED device is not in use. The periodic self-test is preferably administered by execution of software instructions by processor 126 and/or associated device circuitry.

After being placed into operation in a standby condition (i.e., not in use for a cardiac rescue), the defibrillator automatically conducts a self-test upon a predetermined schedule. Exemplary schedules are daily, weekly, and monthly tests, although the exact nature and schedule of tests may vary. The self-test is triggered by on-board clock 122 and is preferably controlled by software instructions executed by hardware processor 126 and self-test circuit 120.

The periodic self-tests are designed for the purpose of detecting a fault in AED 100 circuitry, wherein the self-test outcome may comprise either a "ready for use" condition or a fault condition. A common result of the self-test is a determination of "ready for use", i.e. no fault is determined. AED 100 then powers down and returns to the low-power standby condition. AED 100 provides some sort of indication that the device is ready for use. An exemplary ready condition is a flashing "ready" light with no audio output. A sensed press of the information button 102 (i.e., the i-button) in this state may initiate an audible or displayed status message such as "ready for use."

If defibrillator/AED 100 detects one or more device faults, then an alarm is issued according to an alarming protocol for the device. For example, an audible annunciator may provide a loud chirp or series of chirps during a fault condition that alerts anyone in the vicinity that the AED 100 is not fully operable. Some faults, such as a low battery, may not render the device fully inoperable. In such cases a single chirp may be issued on a second periodicity such as every 6 seconds. Other faults, such as a defibrillating circuit failure may be fatal, and so a triple chirp may thus be issued from output 104 along with a flashing light from visual output 108. Information about the fault may be displayed on display 112. The visual and audible alarms preferably continue at the second periodicity until the fault is corrected or all of the battery power is consumed.

Figure 4:
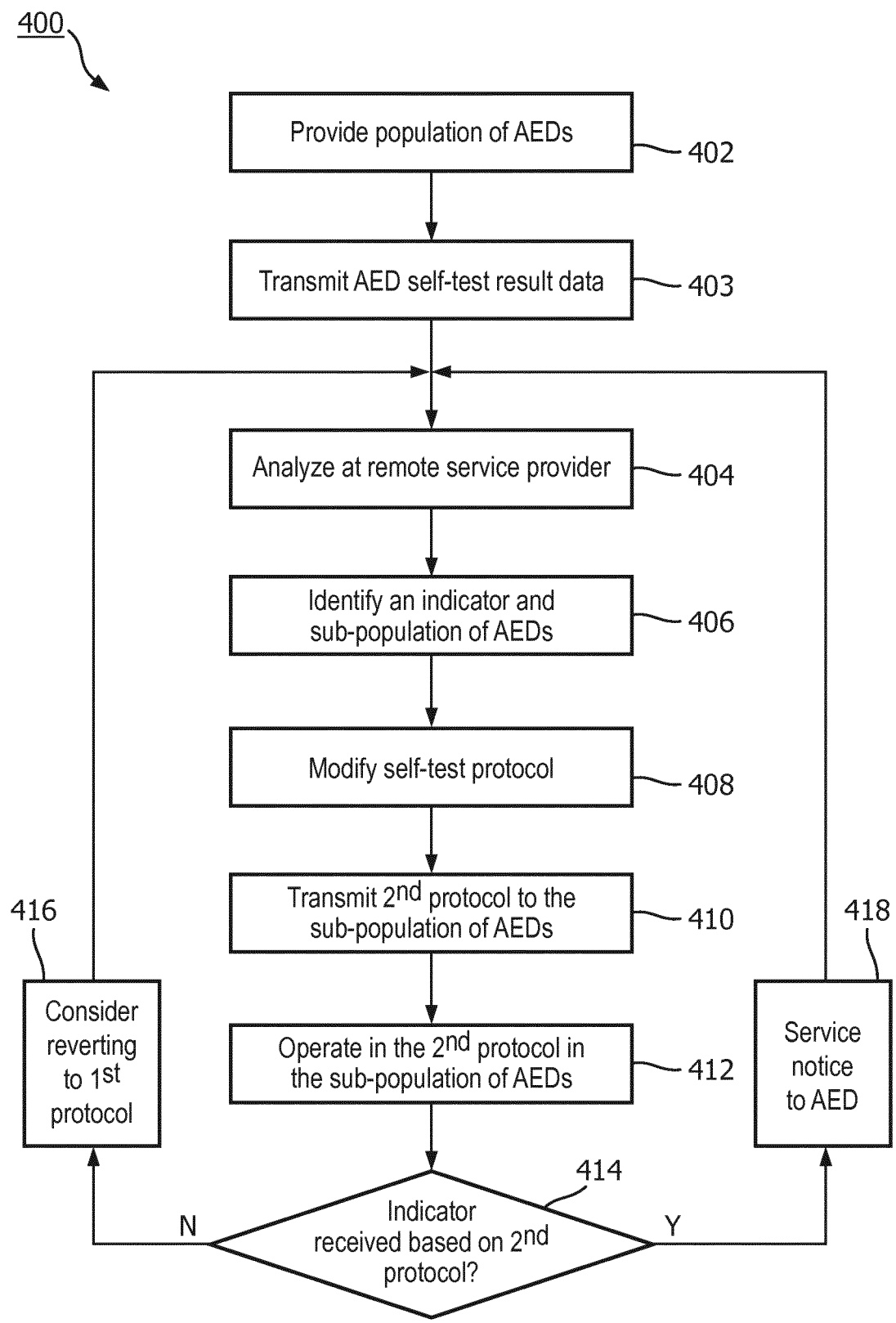
FIG. 4 is a flow diagram view of a method of predictive diagnostics in a distributed population of AED devices according to another embodiment of the present disclosure.

Referring now to FIG. 4, there is shown a flow diagram view of a method 400 of predictive diagnostics in a distributed population of AED devices according to another embodiment of the present disclosure. The method for predictive diagnostics in a distributed population of automated external defibrillator (AED) devices comprises the steps of providing a plurality of AED devices (Step 402), transmitting AED functional measurement values and AED self-test result data to the remote service provider (Step 403), analyzing the AED functional measurement values and AED self-test result data received from the plurality of AED devices at the remote service provider (Step 404), identifying at least one indicator of an impending fault or failure that is predictive of an impending AED fault or failure in at least one non-failed AED of the plurality of AEDs based on the analyzed periodic functional measurement values and AED self-test result data (Step 406), and remotely modifying the self-test protocol via obtaining a second protocol for executing a second AED self-test on a sub-set or sub-population of the plurality or population of AEDs based upon the identified at least one indicator (Step 408), transmitting the second protocol to the sub-population of AEDs (Step 410), operating in the second protocol in the sub-population of AEDs (Step 412), querying whether an indicator has been received based on the second protocol (Step 414), and responsive to no receipt of an indicator based on the second protocol, proceeds by considering whether to revert to the first protocol (Step 416) followed by returning to Step 404 of analyzing at the remote service provider (Step 404) and proceeding as previously discussed. On the other hand, responsive to receipt of an indicator based on the second protocol, the method proceeds from the query (Step 414) by transmitting a service notice to the AED (Step 418) followed by returning to Step 404 of analyzing at the remote service provider (Step 404) and proceeding as previously discussed. In Step 402, each AED comprises (i) an automated self-testing controller for testing a readiness of the respective AED, via an AED self-test, on a periodic basis, (ii) a memory storage location for storing software instructions, executable by the automated self-testing controller, the software instructions including a protocol for executing the AED self-test, the memory storage location further for storing (ii)(a) functional measurement values obtained via the AED self-test and (ii)(b) an AED self-test result, and (iii) a bi-directional transceiver configured to transmit the functional measurement values and the AED self-test result and to receive information that pertains to one or more of the periodic AED self-tests, wherein the information comprises at least software instructions including a second protocol for executing a second AED self-test. The method further includes, automatically replacing, via the automated self-testing controller of the AED, the protocol with the second protocol in the memory storage location.

In Step 404, the analyzing is accomplished via a remote service provider computer provided with a bi-directional transceiver configured to receive and transmit information that relates to the periodic AED self-tests of the plurality of AED devices. The AED self-test result data includes functional measurement values obtained via the periodic AED self-tests. The AED self-test result data further includes data from at least one failed AED device of the plurality of AED devices. In Step 406, the identifying is accomplished via the remote service provider computer. In Step 408, the remotely modifying the protocol for executing the at least one AED self-test of the sub-set is accomplished via the remote service provider computer. The remote modification of the protocol is configured to pre-empt an occurrence of a failure outcome of an AED self-test in the AED devices of the sub-set of the plurality of AED devices. In other words, the various steps 404 to 410 are performed via the remote service provider computer 14 executing instructions programmed (i) to analyze the AED functional measurement values and the self-test results, wherein the AED self-test results further include data from at least one failed AED of the plurality of AEDs, (ii) to identify at least one indicator of an impending fault or failure that is predictive of an impending AED device fault or failure in a sub-set of the plurality of AEDs based on the analyzed periodic AED self-test result data, and (iii) to obtain the second protocol for executing the second AED self-test of a sub-set of the plurality of AEDs, based upon the identified at least one indicator. As discussed, the AED self-test result data received from the plurality of AEDs includes functional measurement values of periodic AED self-tests and further includes data from at least one failed AED device of the plurality of AEDs. Modifying the self-test protocol includes obtaining the second protocol for executing the second AED self-test in the sub-set of the plurality of AED devices, based upon the identified at least one indicator, which pre-empts an occurrence of a failure outcome of an AED self-test in the AEDs of the sub-set or sub-population of the plurality or population of AEDs. The remote service provider computer further executes instructions programmed (iv) to transmit software instructions including the second protocol for executing the second AED self-test to only the sub-set of the plurality of AEDs.

According to yet another embodiment, a non-transitory computer-readable medium embodied with a computer program of instructions executable by a computer for carrying out the method of predictive diagnostics in a distributed population of automated external defibrillator (AED) devices, as discussed herein.

As discussed herein, the various embodiments of the device health monitoring system of the present disclosure advantageously provide an improved reliability or safety feature to a population of AED devices. The embodiments have application to AEDs and advanced defibrillators with the capability to send diagnostic self test data to a remote central server (RCS).

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A predictive diagnostic system for a distributed population of automated external defibrillators (AEDs), the predictive diagnostic system comprising:
    a plurality of AEDs, wherein each AED includes;
        (i) an automated self-testing controller for testing a readiness of the respective AED via a first periodic AED self-tests,
        (ii) a memory storage location for storing software instructions, executable by the automated self-testing controller, the software instructions including a first protocol for executing the first periodic AED self-tests by the automated self-testing controller, the memory storage location further for storing (ii) (a) functional measurement values and (ii) (b) AED self-test results obtained from an execution of the first periodic AED self-tests via the first protocol by the automated self-testing controller, and
        (iii) an AED bi-directional transceiver configured to transmit the functional measurement values and the AED self-test results of the first periodic AED self-tests as stored in the memory storage location and to receive software instructions including a second protocol for executing a second periodic AED self-tests by the automated self-testing controller, the automated self-testing controller operable to automatically replace the first protocol with the second protocol in the memory storage location; and
    a remote service provider computer provided with a bi-directional transceiver configured to receive and transmit information that pertains to the first periodic AED self-tests of the plurality of AEDs, wherein the remote service provider computer is programmed to:
        (i) analyze the functional measurement values and the AED self-test results of the first periodic AED self-tests received from the plurality of AEDs, wherein the AED self-test results of the first periodic AED self-tests further include data from at least one failed AED of the plurality of AEDs;
        (ii) identify at least one indicator of an impending fault or failure that is predictive of an impending AED fault or failure in a sub-set of the plurality of AEDs based on an analysis by the remote service provider computer of the functional measurement values and the AED self-test results of the first periodic AED self-tests received by the remote service provider computer from the plurality of AEDs, (iii) obtain the second protocol for executing the second periodic AED self-tests of the sub-set of the plurality of AED devices, based upon an identification of the at least one indicator by the remote service provider computer, to pre-empt an occurrence of a failure outcome of the second periodic AED self-tests in the AEDs of the sub-set of the plurality of AEDs; and (iv) to transmit the software instructions including the second protocol for executing the second periodic AED self-tests to only the sub-set of the plurality of AEDs; and wherein, upon receipt of the software instructions including the second protocol by the AED bi-directional transceivers of the sub-set of the plurality of AEDs, the automated self-testing controller of each AED of the sub-set of the plurality of AEDs automatically replaces the first protocol with the second protocol in the memory storage location of each AED of the sub-set of the plurality of AEDs for executing the second periodic AED self-tests.

2. The predictive diagnostic system of claim 1, wherein the indicator includes a data signature of the functional measurement values of the at least one AED ($12_{N-2}$ to $12_N$) of the plurality of AEDs which has failed, or a data trend of the functional measurement values of the at least one AED of the plurality of AEDs which has failed.

3. The predictive diagnostic system of claim 2, wherein the remote service provider computer is further programmed to determine the sub-set of the plurality of AEDs in response to at least one non-failed AED of the plurality of AEDs having a data signature matching, by at least a given percentage, the data signature of the at least one AED which has failed; or a data trend matching, by at least a given percentage, the data trend of the at least one AED which has failed.

4. The predictive diagnostic system of claim 1, wherein the remote service provider computer is further programmed to transmit, one or more of:
(i) a notification, self-test command, or instruction directly to a respective AED of the sub-set of the plurality of AEDs to signal an alert at the respective AED of a corresponding impending fault or failure; and
(ii) a notification directly to a registered administrator of the respective AED of the corresponding impending fault or failure.

5. The predictive diagnostic system of claim 1, wherein the functional measurement values relate to an electrical resistor (R) component in an AED.

6. The predictive diagnostic system of claim 5,
wherein the functional measurement values include voltage measurements across the resistor (R), wherein the voltage measurements across the resistor indicate a likelihood of impending failure after a subsequent given number of energy pulses applied during a corresponding AED self-test of a given AED; and
wherein the remote service provider computer is further programmed to analyse the functional measurement values for a degrading voltage measurement over time, which by itself would not result in a self-test failure outcome, to identify the at least one indicator of an impending fault or failure.

7. A method for predictive diagnostics in a distributed population of automated external defibrillators (AEDs), the method comprising the steps of:
providing a plurality of AEDs, wherein each AED includes:

(i) an automated self-testing controller for testing a readiness of the respective AED device, via a first periodic AED self-tests;
(ii) a memory storage location for storing software instructions, executable by the automated self-testing controller, that include at least a first protocol for executing the first periodic AED self-tests, the memory storage location further for storing (ii) (a) functional measurement values, and (ii) (b) AED self-test results obtained from an execution of the first periodic AED self-tests via the first protocol by the controller; and
(iii) an AED bi-directional transceiver configured to transmit the functional measurement values and the AED self-test results of the first periodic AED self-tests and to receive software instructions including a second protocol for executing second periodic AED self-tests, the automated self-testing controller operable to automatically replace the first protocol with the second protocol in the memory storage location;

analyzing, via a remote service provider computer with a bi-directional transceiver configured to receive and transmit information that pertains to the first periodic AED self-tests of the plurality of AEDs, the functional measurement values and the AED self-test results of the first periodic AED self tests received from the plurality of AEDs, and wherein the AED self-test results include data from at least one failed AED of the plurality of AEDs;

identifying, via the remote service provider computer, at least one indicator of an impending fault or failure that is predictive of an impending AED fault or failure in at least one non-failed AED of the plurality of AEDs based on the functional measurement values and the AED self-test results of the first periodic AED self-tests received by the remote service provided computer from the plurality of AEDs;

modifying, via the remote service provider computer, the first protocol to a second protocol for executing second periodic AED self-tests of a sub-set of the plurality of AEDs based upon the identified at least one indicator, to pre-empt an occurrence of a failure outcome of an AED self-test in the AEDs of the sub-set of the plurality of AEDs;

transmitting software instructions including the second protocol for executing the second periodic AED self-tests to only the sub-set of the plurality of AEDs; and executing, by the sub-set of the plurality of AEDs, the second periodic AED self-tests using the transmitted software instructions.

8. A non-transitory computer-readable medium embodied with a computer program of instructions executable by a computer for carrying out the method of predictive diagnostics in a distributed population of automated external defibrillators (AEDs) according to claim 7.

9. An automated external defibrillator (AED) for use in a predictive diagnostic system for a distributed population of automated external defibrillators (AEDs), the automated external defibrillator (AED) comprising:
an automated self-testing controller for testing a readiness of the AED, via first periodic AED self-tests;
a memory storage location for storing software instructions, executable by the automated self-testing controller, that include a first protocol for executing the first periodic AED self-tests, the memory storage location further for storing (ii) (a) functional measurement values and (ii) (b) AED self-test result obtained via the first AED self-tests executed by the automated self-testing controller;

a bi-directional transceiver configured to transmit the functional measurement values and the first AED self-test results to a remote service provide computer and to receive software instructions from the remote service provide computer including a second protocol for executing second periodic AED self-tests by the automated self-testing controller when the functional measurement values and the AED self-test results of the first periodic AED self-tests indicate an impending fault or failure in the AED, wherein the automated self-testing controller is configured to execute the second periodic AED self-tests upon receipt of the second protocol; and an output controllably connected to the automated self-controlling controller and configured to indicate which of the first periodic AED self-tests and the second periodic AED self-tests are in use.

10. The automated external defibrillator (AED) of claim 9, wherein the output includes one selected from the group of; a defibrillator display, an audible output and a visual status light.

11. The automated external defibrillator (AED) of claim 10, further comprising:

an information button input in communication with the controller, the controller configured to provide detailed AED self-test information relating to the first and the second AED self-test to the user via the output.

12. The automated external defibrillator (AED) of claim 9, wherein the output further indicates that the AED is ready for use and that user action to contact an AED service provider is requested.

* * * * *